US00PP21301P2

(12) United States Plant Patent
des Brisay

(10) Patent No.: US PP21,301 P2
(45) Date of Patent: Sep. 21, 2010

(54) ***CENTRADENIA* PLANT NAMED 'BLUSHING CASCADE'**

(50) Latin Name: *Centradenia inaequilateralis*
Varietal Denomination: Blushing cascade

(76) Inventor: Junius des Brisay, Corner Cottage, Buriton, Petersfield, Hampshire (GB) GU31 5RZ ( * ) Notice: Subject to any disclaimer, the term of this patent is extended or adjusted under 35 U.S.C. 154(b) by 0 days.

(21) Appl. No.: 12/386,744

(22) Filed: Apr. 21, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para

(57) ABSTRACT

A new and distinct cultivar of *Centradenia* plant named 'BLUSHING CASCADE' that is characterized by light-pink flowers and diminutive red buds, long bloom period, and green foliage infused with red highlights. In combination these traits set 'BLUSHING CASCADE' apart from all other existing varieties of *Centradenia* known to the inventor.

2 Drawing Sheets

Genus: *Centradenia.*
Species: *inaequilateralis.*
Denomination: 'BLUSHING CASCADE'.

BACKGROUND OF THE INVENTION

The present invention relates to a new and distinct cultivar of *Centradenia* grown as an ornamental perennial for use in containers and hanging baskets, and as a shrub for the garden and landscape. The new invention from the family Melastomataceae is known botanically as *Centradenia inaequilateralis* and will be referred to hereinafter by the cultivar name 'BLUSHING CASCADE'.

'BLUSHING CASCADE' was discovered in 1998 as a naturally occurring branch sport found growing on a single plant of *Centradenia* 'Cascade' (unpatented). The sport parent, 'Cascade', was growing in the inventor's nursery in Petersfield, Hampshire, United Kingdom. The inventor observed that the sported branch bore light pink flowers whereas the flowers of 'Cascade' are red-purple in color. The inventor made softwood cuttings from the sporting branch and established such asexually reproduced plants on their own roots. Once the inventor was able to observe fully grown whole plants of 'BLUSHING CASCADE' the inventor concluded that 'BLUSHING CASCADE' also exhibited brighter colored foliage, a stronger plant habit and a longer flowering season when compared with the parent 'Cascade'. The inventor is not aware of any other varieties of *Centradenia* that resemble 'BLUSHING CASCADE' other than the parent variety, 'Cascade'.

The first asexual propagation of 'BLUSHING CASCADE' was conducted by the inventor in Hampshire, United Kingdom. Asexual propagation was accomplished in 1998 at the inventor's nursery. The method used was softwood cuttings. Since that time under careful observation 'BLUSHING CASCADE' has been determined fixed, stable, uniform, and to reproduce true to type in subsequent generations of asexual propagation.

SUMMARY OF THE INVENTION

The following traits have been repeatedly observed and represent the distinguishing characteristics of the new *Centradenia* cultivar named 'BLUSHING CASCADE'. These traits in combination set 'BLUSHING CASCADE' apart from all other existing varieties of *Centradenia* known to the inventor. 'BLUSHING CASCADE' has not been tested under all possible conditions and phenotypic differences may be observed with variations in environmental, climatic, and cultural conditions without however any variance in genotype.

1. 'BLUSHING CASCADE' bears a large number of light-pink flowers. During bloom period, diminutive red buds are present, the combination of which creates a pronounced ornamental effect.
2. 'BLUSHING CASCADE' exhibits a long flowering season, winter through spring in frost-free zones.
3. 'BLUSHING CASCADE' exhibits compact habit.
4. 'BLUSHING CASCADE' exhibits red stems.
5. 'BLUSHING CASCADE' exhibits green foliage infused with red highlights.
6. 'BLUSHING CASCADE' reaches 32 cm. in height and 77 cm. in width at maturity.
7. 'BLUSHING CASCADE' is hardy at least in USDA Zone 8.

BRIEF DESCRIPTION OF THE DRAWINGS

The accompanying color drawings illustrate the overall appearance of the new *Centradenia* cultivar named 'BLUSHING CASCADE' showing the color as true as is reasonably possible to obtain in color reproductions of this type. Color in the drawings may differ from color values cited in the detailed botanical description, which accurately describe the actual color of the new variety 'BLUSHING CASCADE'. Drawings are of plants that are greenhouse grown.

The drawing labeled

The drawing labeled

Figure 1:
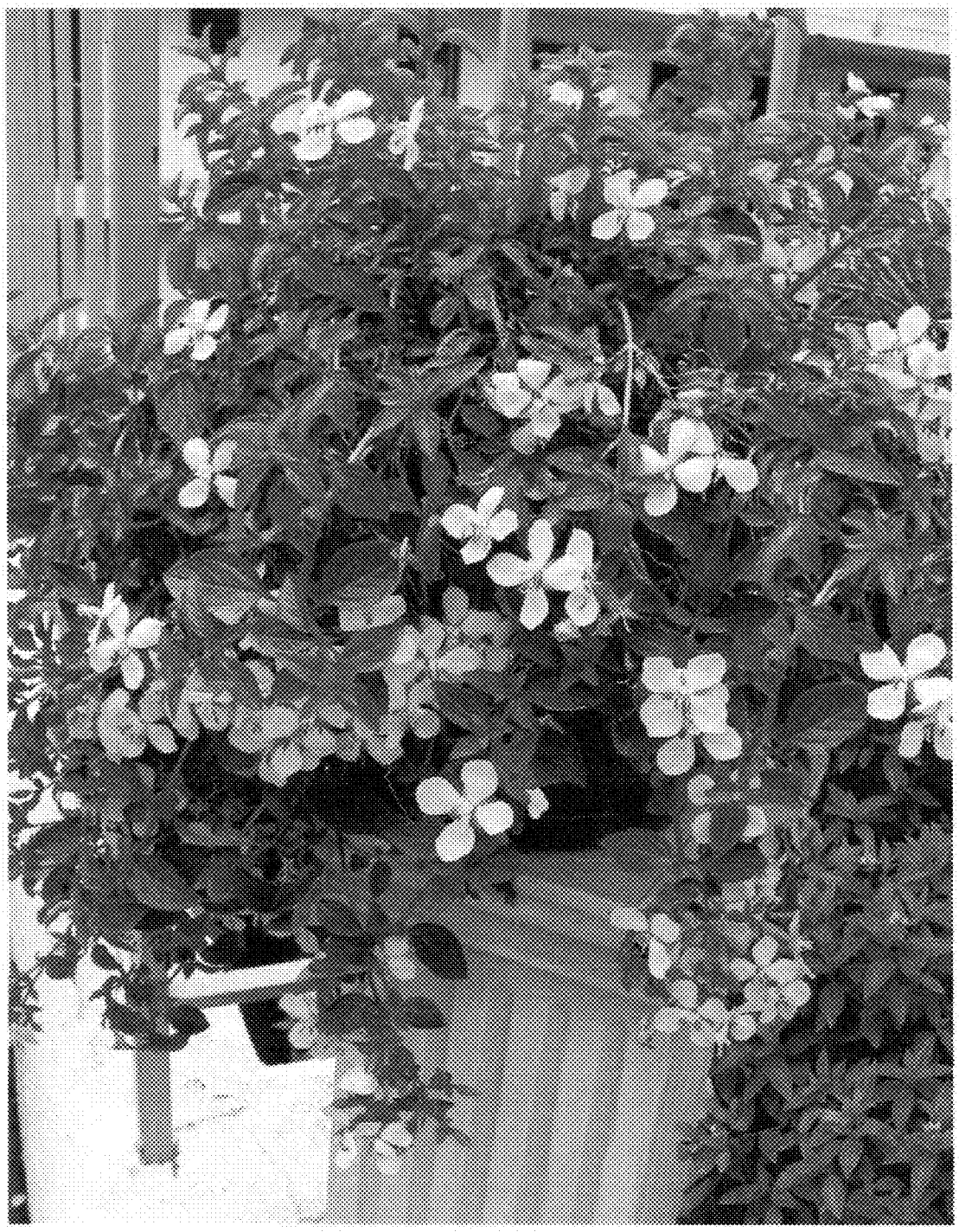
FIG. 1 illustrates a plant of 'BLUSHING CASCADE' growing in an 8 inch container out of doors in Santa Barbara, Calif. The illustrated plant is approximately 15 months of age.
Figure 2:
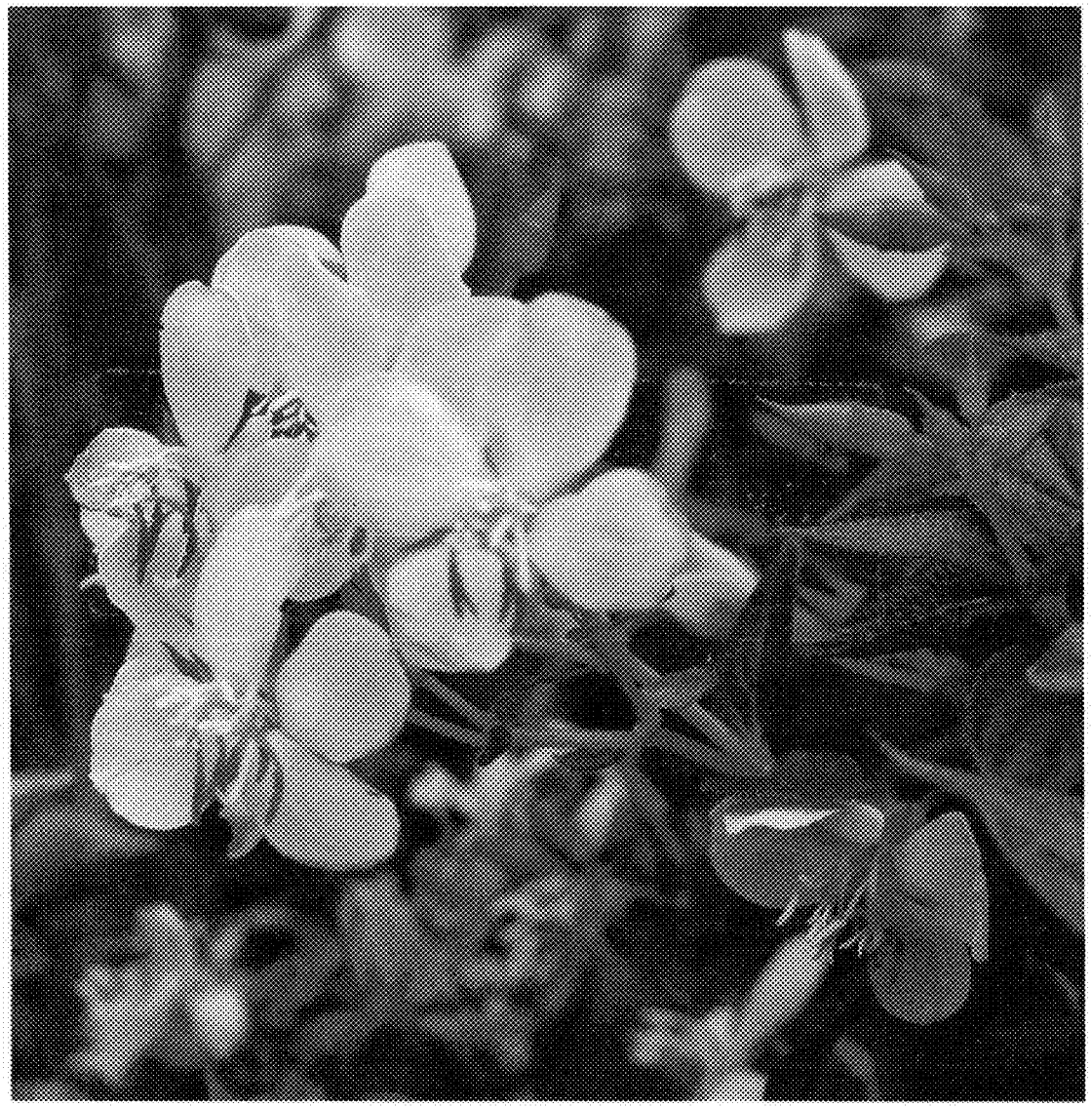
FIG. 2 illustrates a close-up view of the light pink flowers and diminutive red buds of the plant shown in FIG. 1.

Both drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Centradenia* cultivar named 'BLUSHING CASCADE'. Observations, measurements, values and comparisons were collected in Arroyo Grande, Calif., from 18-month-old plants grown out-of-doors in 2-liter containers. Color determinations are made in accordance with the 2001 Royal Horticultural Society Colour Chart from London, England, except where general color terms of ordinary dictionary significance are used. The growing requirements of the new variety 'BLUSHING CASCADE' are similar to the species.

Botanical classification: *Centradenia inaequilateralis* 'BLUSHING CASCADE'.
Family: Melastomataceae.
Genus: *Centradenia*.
Species: *inaequilateralis*.
Denomination: 'BLUSHING CASCADE'.
Common name: *Centradenia*.
Habit: Compact.
Commercial category: Sub-shrub.
Use: For garden and landscape.
Suggested commercial container size: 1-liter container.
Parentage: *Centradenia inaequilateralis* 'BLUSHING CASCADE' was discovered as a sport derived from the following parent:
*Parent.*—An individual *Centradenia* 'Cascade' (unpatented).
Propagation method: Vegetative cuttings.
Rooting system: Fine.
Vigor: Vigorous.
Crop time (range): 6-9 months to produce a 1-liter container from stem cuttings.
Temperature (range): The recommended air temperature is 20-21° Centigrade.
Plant dimensions (first year): 32 cm. in height and 36 cm. in width.
Plant dimensions (at maturity): 36 cm. in height and 77 cm. in width.
Cultural requirements: Grow in filtered light or partial shade, sandy loam soil, with regular to plentiful water.
Pest or disease resistance: None known to the inventor.
Pest or disease susceptibility: None known to the inventor.
Hardiness: USDA Zone 8.
Special considerations: Pinch back to encourage branching. Give plentiful water during growing season.
Stem:
*Shape.*—Quadrangular.
*Surface* (*abaxial and adaxial*).—Sericeous.
*Color.*—178A.
*Length* (*range*).—25-48 cm.
*Diameter* (*range*).—3 mm-0.40 cm.
*Internode* (*range*).—1-5 cm.
Foliage:
*Type.*—Evergreen.
*Arrangement.*—Opposite.
*Division.*—Simple.
*Margin.*—Entire.
*Surface* (*abaxial and adaxial*).—Sericeous.
*Shape.*—Ovate.
*Length* (*range*).—2.50-3.50 cm.
*Width* (*range*).—1.50-1.75 cm.
*Color* (*abaxial surface*).—147A infused with highlights of 59A.
*Color* (*adaxial surface*).—147A infused with highlights of 59A.
*Apex.*—Acute.
*Base* (*range*).—Rounded to aequilateral.
*Venation.*—Pinnate.
*Vein color* (*abaxial and adaxial surfaces*).—147D.
*Attachment.*—Petiolate.
*Petiole shape.*—Sulcate.
*Petiole surface.*—Sericeous.
*Petiole color.*—178A.
*Petiole dimensions.*—6 mm. in length and 2 mm. in width.
*Leaf fragrance.*—None observed.
Inflorescence:
*Type.*—Axillary panicle.
*Aspect.*—Facing upward and outward.
*Bloom season.*—Winter through spring in frost-free zones.
*Bud shape.*—Nutlet-shaped.
*Bud color.*—53A.
*Bud length* (*range*).—6 mm. to 1 cm.
*Bud width* (*range*).—2 mm. to 0.40 cm.
*Bud apex.*—Narrow acute.
*Bud base.*—Rounded.
*Bud surface.*—Bullate.
*Bud quantity.*—>100 per 1-liter container plant.
*Flower quantity.*—>50 per 1-liter container plant.
*Flower shape.*—Rotate.
*Flower dimensions.*—2 cm. in depth and 3.25 cm. in diameter.
*Petal.*—4 in number.
*Petal shape.*—Obovate.
*Petal color.*—75A.
*Petal margin.*—Entire.
*Petal apex.*—Obovate.
*Petal surface* (*abaxial and adaxial*).—Glabrous.
*Petal length.*—1.40 cm.
*Petal width.*—1.25 cm.
*Petals fused or unfused.*—Unfused.
*Hypanthium dimensions.*—0.60 cm. in height and 0.50 cm. in diameter.
*Hypanthium surface* (*dorsal*).—Bullate.
*Hypanthium color.*—N34C.
*Calyx shape.*—Stellate.
*Calyx color.*—47A.
*Sepal.*—4 in number.
*Sepal shape.*—Lanceolate.
*Sepal margin.*—Entire.
*Sepal surface* (*abaxial and adaxial*).—Glabrous.
*Sepal apex.*—Apiculate.
*Sepal base.*—Truncate.
*Sepal fused or unfused.*—Unfused.
*Sepal dimensions.*—8 mm. in length and 5 mm. in width.
*Sepal color* (*abaxial and adaxial surface*).—47A.
*Persistent or self-cleaning.*—Self-cleaning.
*Peduncle color.*—47A.
*Peduncle dimensions* (*average*).—0.70 cm. in length and <1 mm. in width.
*Peduncle shape.*—Quadrangular.
*Peduncle surface.*—Sericeous.
*Inflorescence fragrance.*—None observed.
*Lastingness of inflorescence.*—Ephemeral.

Reproductive organs:

*Stamen quantity.*—8 unequal stamens.

*Stamen length* (*range*).—8-9 mm.

*Stamen color.*—N155C.

*Anther color.*—4 anthers are 71C. 4 anthers are 1B.

*Anther length* (*range*).—3-9 mm.

*Pollen amount.*—Low.

*Pollen color.*—71D.

*Spur.*—4 in number.

*Spur dimensions.*—3 mm. in length and <2 mm. in width.

*Spur color.*—86A.

*Spur surface.*—Rugose.

*Pistil quantity.*—1 in number.

*Pistil length.*—7 mm.

*Pistil color.*—N155C.

*Stigma dimensions.*—<1 mm. in height and <1 mm. in width.

*Stigma shape.*—Tapered.

*Stigma color.*—N155C.

*Ovary position.*—Inferior.

*Ovary shape.*—Urceolate.

*Ovary dimensions.*—6 mm. in height and 4 mm. in width.

*Ovary color.*—142D.

Seed: No seed has been observed.

It is claimed:

1. A new and distinct cultivar of *Centradenia* plant named 'BLUSHING CASCADE' as described and illustrated herein.

* * * * *